US008233631B2

(12) United States Patent
Berzanskis

(10) Patent No.: US 8,233,631 B2
(45) Date of Patent: Jul. 31, 2012

(54) MEDIC VOICE DATA SYSTEM

(75) Inventor: Audrius Berzanskis, Cambridge, MA (US)

(73) Assignee: MagiQ Technologies, Inc., Somerville, MA (US)

( * ) Notice: Subject to any disclaimer, the term of this patent is extended or adjusted under 35 U.S.C. 154(b) by 288 days.

(21) Appl. No.: 12/798,974

(22) Filed: Apr. 15, 2010

(65) Prior Publication Data

US 2011/0103597 A1     May 5, 2011

Related U.S. Application Data

(60) Provisional application No. 61/268,477, filed on Jun. 12, 2009.

(51) Int. Cl.
*A61B 7/04* (2006.01)
(52) U.S. Cl. ......................................................... 381/67
(58) Field of Classification Search .................... 381/67, 381/77, 94.1, 71.1
See application file for complete search history.

(56) References Cited

U.S. PATENT DOCUMENTS

| 6,781,522 B2 * | 8/2004 | Sleva et al. ................. 340/870.1 |
| 2008/0298603 A1 * | 12/2008 | Smith ............................. 381/67 |
| 2011/0178359 A1 * | 7/2011 | Hirschman et al. ............... 600/4 |

* cited by examiner

*Primary Examiner* — Ping Lee
(74) *Attorney, Agent, or Firm* — Opticus IP Law PLLC

(57) ABSTRACT

A medical voice data system includes a hand-held recording device, an electronic information carrier (EIC), and a host station. The hand-held device records medical information from a user that is examining a person in an extreme environment such as battlefield or disaster area. EICs are stored within a housing interior and can be dispensed therefrom by the user. Recording electronics within the housing interior are operably connected to at least one of the EICs. A microphone is operably connected to the recording electronics to record on a EIC medical information about the injured person. The EIC is configured to be attached to and travel with the person as they are evacuated so that the recorded medical information is immediately available to medical personnel at a care center via the host station. The medical voice data system may also employ a wireless EIC. A host station is used to receive and process the recorded information and convert it to text-based medical record.

11 Claims, 13 Drawing Sheets

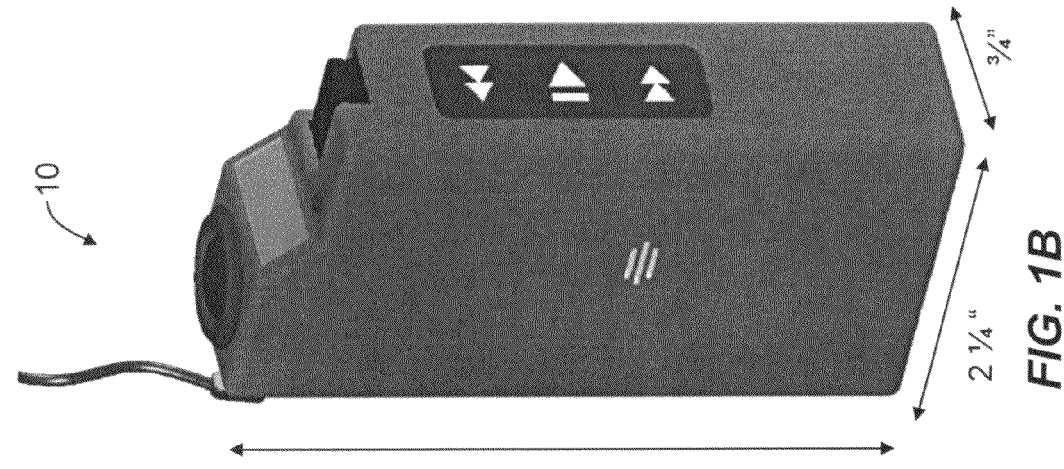
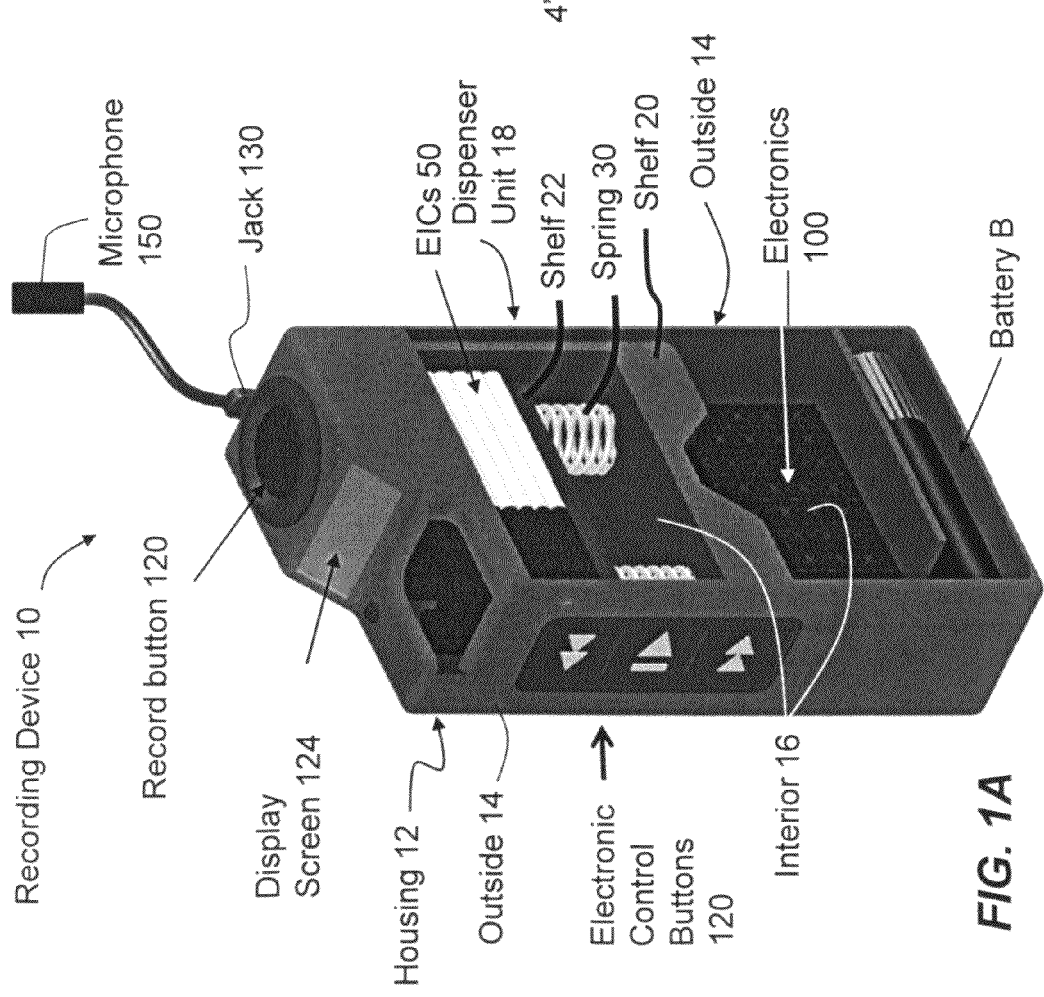

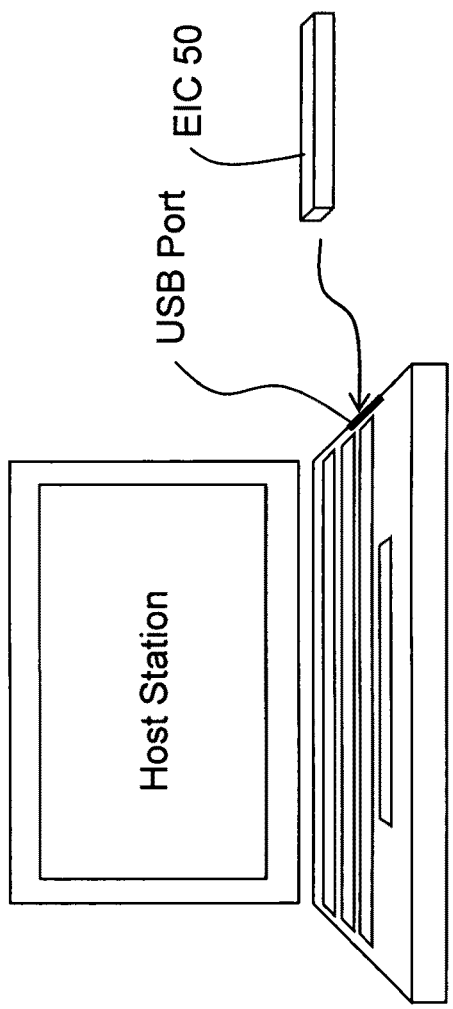
FIG. 5A
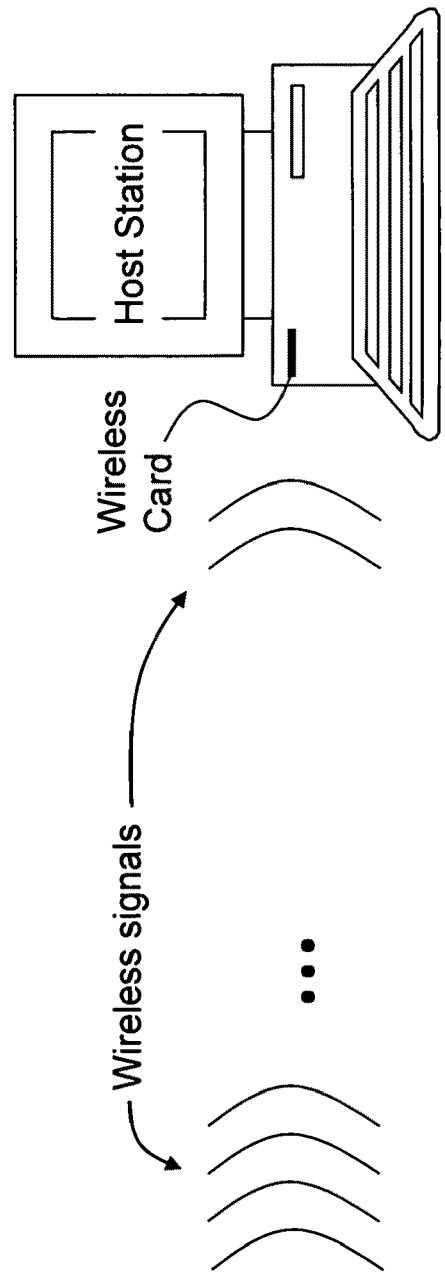
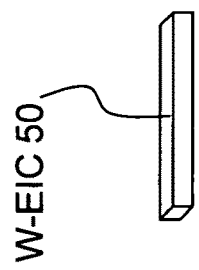
FIG. 5B

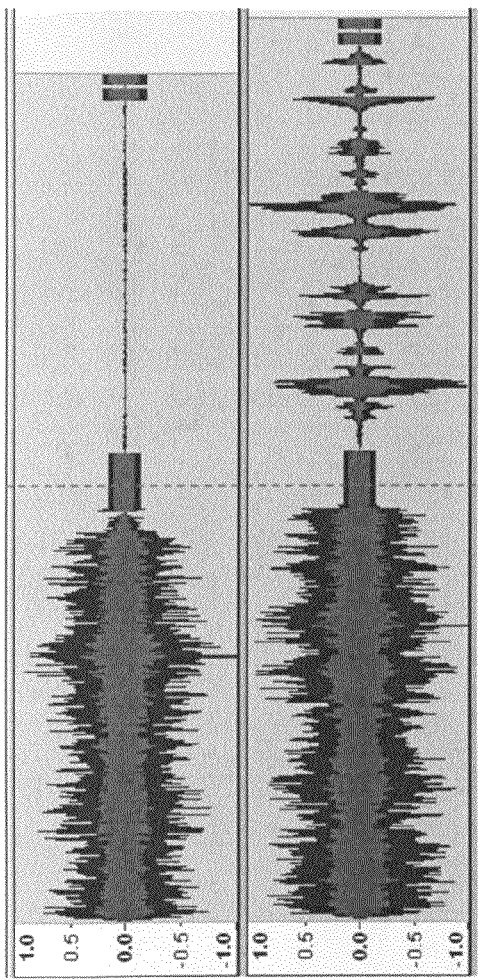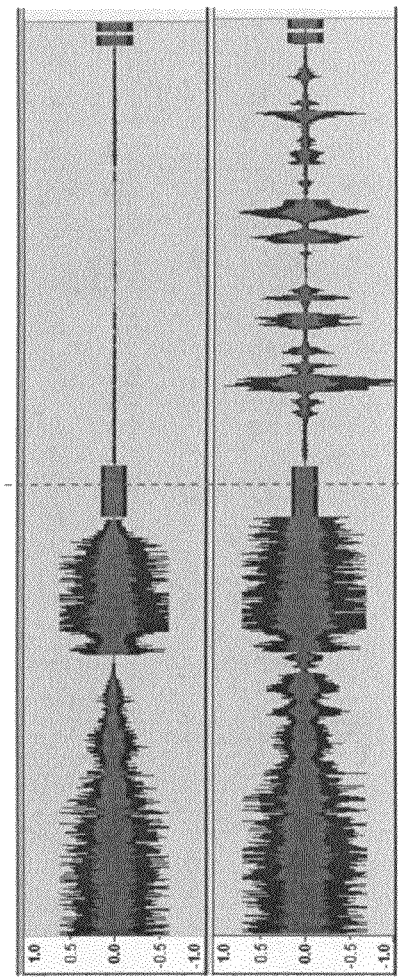
FIG. 9B

MEDIC VOICE DATA SYSTEM

CLAIM OF PRIORITY

This application claims the benefit of priority under 35 U.S.C. §119(e) of U.S. Provisional Application Ser. No. 61/268,477, filed on Jun. 12, 2009, and which is incorporated by reference herein.

FIELD

The present invention relates generally to medical data systems, and in particular to such systems for recording and processing medical information in extreme environments.

BACKGROUND ART

Caring for the critically wounded in extreme environments requires accurate documentation of the nature of the injury and the treatment given to the person by the first responder or medic close to the point of injury. It is a challenge to quickly and efficiently record medical information about injured personnel in extreme environments such as battlefields, urban areas or disaster areas. Medical personnel need to be able to examine an injured person and quickly record all of the relevant medical information in a noisy and potentially dangerous environment. Such medical personal need to have their hands free when examining the injured person, and also need to be able to leave the medical information with the injured person and move quickly to the next injured person. Further, the recording device used to record the medical information needs to be hardened for the harsh environmental conditions associated with extreme environments.

There already exist computer-based data-entry medical recording systems for battle field use. Unfortunately, these systems are not widely used because of their relative complexity.

Thus, there is a need for a mobile medical information data system suitable for use in extreme environments that will allow medical personnel to quickly and efficiently record medical information about injured persons, and have the recorded information travel with the injured person, and then have the information processed at a care center or other location.

SUMMARY OF THE INVENTION

A medic voice data system (MVDS) includes a mobile recording device, at least one electronic information carrier (EIC) stored in the recording device and that records information from the recording device and that is removable from the recoding device, and a host station adapted to read information from the EIC either directly through a communications port (e.g., a USB port) or wirelessly (e.g., via a wireless card).

The recording device includes a housing having an outside and that defines an interior. A plurality of EICs are removably stored within the housing interior. The EICs may include wireless capability. Recording electronics are stored within the housing interior and are operably connected to at least one of the EICs. The EICs are movable so that when one EIC is dispensed from the device, another EIC takes its place and is ready to receive and store medical information. A microphone is arranged either on or operably connected to the housing and operably connected to the recording electronics so as to record on one of the EICs the medical information about the injured person. The device is particularly well suited for extreme environments such as a battlefield, disaster areas or urban areas. Example devices include noise cancellation electronics configured to remove ambient noise in the environment so that the recorded medical information can be heard more clearly when the information is played back on a host station.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description present embodiments of the invention, and are intended to provide an overview or framework for understanding the nature and character of the invention as it is claimed. The accompanying drawings are included to provide a further understanding of the invention, and are incorporated into and constitute a part of this specification. The drawings illustrate various embodiments of the invention, and together with the description serve to explain the principles and operations of the invention.

BRIEF DESCRIPTION OF THE DRAWINGS

FIG. 1A and FIG. 1B are perspective views of the recorder device according to the present invention;

FIG. 5A illustrates an example host station in the form of a laptop computer and how the EIC plugs into the USB port of the laptop computer;

FIG. 5B illustrates an example host station in the form of a personal computer and how the EIC transmits a wireless signal to a wireless card in the personal computer;

FIGS. 9A and 9B are sound plots illustrating examples of using noise cancellation to extract voice information over ambient noise in the extreme environment.

DETAILED DESCRIPTION OF THE INVENTION

Figure 2:
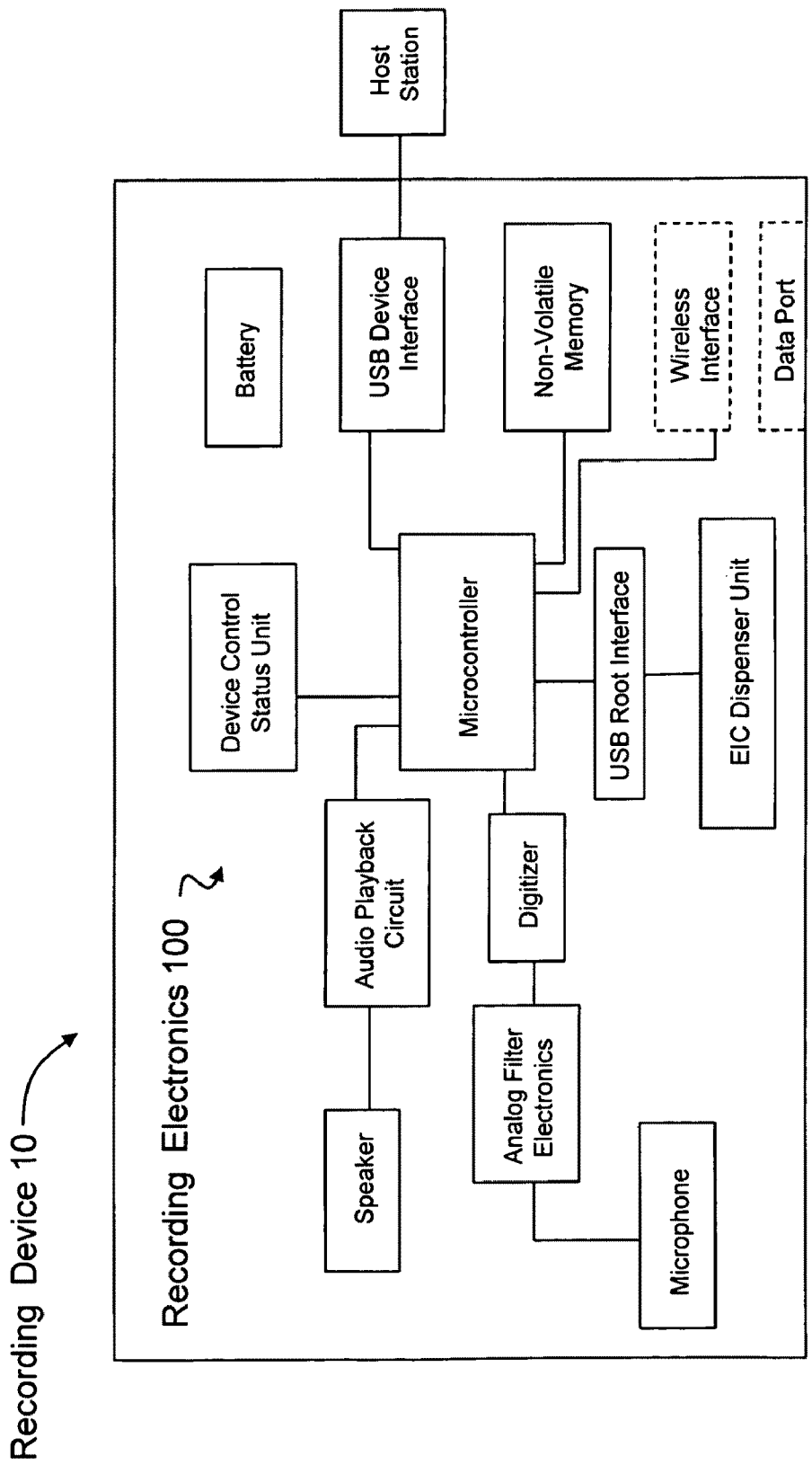
FIG. 2 is a schematic diagram of the recorder device electronics in relation to other components used in Medic Voice Data System (MVDS)

The present invention is directed to a Medic Voice Data System (MVDS) that provides simple, reliable, and unobtrusive tool for users such as medics, nurses, EMTs, etc., so that accurate information can be recorded in an extreme environment such as a battlefield, and then transported and made available to care providers of all levels.

FIG. 1A and FIG. 1B are perspective views of a mobile medical recorder device ("recorder device") 10 according to the present invention. Recorder device 10 is preferably designed to be hand held and used in the field (i.e., a battlefield, disaster areas, urban areas, and like extreme environments) where medical information about people in need of medical attention can be quickly recorded by device users with minimal effort. Medical information about the person being examined and treated includes any number of relevant facts such as blood pressure, heart rate, whether the person is in shock, the nature and severity of any injuries, whether pupils are dilated, whether the person was or is conscious, and a host of other facts and special considerations (e.g., blood type, whether the person is diabetic, allergic to certain medications, etc.).

In one embodiment, the medical information is left with the examined person and travels with the person so that other medical personnel, such as emergency care providers at a hospital, have immediate access to the person's medical information. In another embodiment described below, the information is transmitted wirelessly to a host station for processing.

Recorder device 10 includes a strong and sturdy housing 12, such as made from a light-weight but strong metal or a composite material such as KEVLAR. FIG. 1B shows an example configuration and dimensions of housing 12 as being 4"×2.25"×0.75". Housing 12 includes an outside 14 and defines an interior 16 that includes a dispenser unit 18. In an example, dispensing unit 18 includes a first shelf 20 that supports a second shelf 22 by means of springs 30 or other spring-like mechanism. Second shelf 22 is configured to removably support a plurality of EICs 50 that lie flat on the first shelf. As one EIC 50 is removed (dispensed) from housing 12, springs 30 act to push the remaining EICs upward so as to be in position operable to record information. Similar arrangements are contemplated by the present invention that allow one EIC 50 to be placed in a recording position and then be dispensed, and then have another EIC automatically take its place in the recording position.

Recorder device 10 further includes recording electronics 100 operably supported in housing interior 16 and operably connected to one of EICs 50. Housing 12 also includes a battery compartment in interior 16 that operably supports at least one battery B for powering recording electronics 100. Electronic control buttons 120, such as playback, pause, erase, record, etc. are provided on outside 14 of housing 12. Device 10 preferably includes a display screen 124 that displays status information about the device, such as whether it is on or off, whether it is recording information, whether an EIC 50 is in place in dispenser unit 18 for recording information, etc. Display screen 124 is shown as residing on or in an angled portion of housing 12 so that it can be easily read by the device user.

A microphone jack 130 is also provided that electrically connects to recording electronics 100 and that accommodates a microphone 150. In an example embodiment, microphone 150 and/or recording electronics 100 are configured to be voice-activated so that the recorder device user need not have to press the record button to record information on EIC 50. This allows the user (e.g., EMT) to have his or her hands free to take vital signs and collect information from the person they are examining.

Example Microphones

Recording device 10 preferably includes a high-quality microphone 150 that can be worn by the medic and that cancels or otherwise suppresses background noise. Two types of example microphones include contact microphones and noise-canceling boom microphones.

A contact microphone picks up the voice through the vibration of the user's throat or the head bone. The outer shell of the microphone assembly effectively blocks the airborne noise signal from reaching the internal microphone. Among contact microphones, the most popular is the throat microphone. A good throat microphone can suppress airborne noise by 30 dB. Both throat and head bone microphones can be fitted for battlefield use and have comparable performance.

An open-air noise-canceling boom microphone can be worn as part of a headset. In a noise-canceling boom microphone, both unwanted and wanted acoustic signals enter two microphones. The orientation of these two microphones can be arranged to 90° or 180°. One of the microphones points at the operator's mouth and generates vocal and noise signals. The other generates a noise reference. Both signals enter a noise-cancellation circuit that determines and reduces the ambient noise in real time, but preserves the vocal signals made by the microphone user, with up to 20 dB ambient noise reduction. This type of microphone has lower noise cancellation performance than a throat microphone but has better speech recognition performance.

Thus, in an example embodiment, a military grade headset that combines the noise-cancelling headphone with the throat microphone 150 or a noise-cancelling boom microphone 150 can be employed.

Example Recorder Device Electronics

FIG. 2 is a schematic diagram of recorder device 10 and electronics 100 as well as other components of the MVDS. Electronics 100 includes a digitizer electrically connected to microphone 150 through an analog filter circuit, and to a microcontroller. Electronics 100 also includes an audio playback circuit connected to a speaker and to microcontroller. Electronics 100 further includes a USB device interface, a non-volatile memory, a USB device interface, a USB root interface, a device/control status unit, all of which are connected to the microcontroller. The USB root interface is also connected to the EIC dispenser unit. The recorder device electronics 100 are powered by a battery.

Noise-canceling microphone 150 delivers the user's voice to recorder device 10. Analog noise filtering schemes are implemented in the analog filter circuit prior to the digitizing process. The digitizer converts the filtered voice signal to a digital format for recording and further processing. A commodity 16-bit 48 kHz audio digitizer is used for further noise suppression and speech recognition by the host station. The user can verify the digitized voice information via the audio playback circuit, which is connected to the speaker, which can be an earpiece or part of a headset.

The microcontroller is configured to manage the sound file recording and playback sessions. The microcontroller also performs the sensitivity adjustment of the microphone. In an example embodiment, the microcontroller includes a 10 MIPS 8-bit microprocessor with firmware stored on the micro-controller's on-chip memory.

The USB root interface is used during the information recording stage for transferring the digitized information from the microcontroller to EIC 50. During the information playback/verification stage, the sound files on the top EIC 50 can be sent to the audio playback circuit through the USB root interface.

The non-volatile memory stores sound file copies after the information is formatted into a sound file and transferred to EIC 50. This allows the user to retrieve the recorded information after ejecting the EIC 50 from recording device 10.

The USB device interface serves as an auxiliary USB port for "docking" the recorder device 10 to another device, such as the host station or a laptop computer (e.g., an MC4 laptop computer). Information stored in the non-volatile memory can be uploaded to the host station for converting the digitized voice information into an FMC or other Electronic Medical Record formats as a "backup" for the EIC 50.

The device control status unit allows the user to control and monitor recorder device 10 in a virtually hands-free manner. The device control status includes, for example, a power on/off switch with a vibration feedback, and status Light Emitting Diodes (LEDs) as the user interfaces. In an example, the device control status includes some or all of status LCD screen 124, electronic control buttons 120, and like controls and display components.

In an example, the battery includes, for example, one or two AA size alkaline batteries. Two such batteries will provide enough current for twenty-four hours of active operation. Other types of small batteries can also be used. Since the data can be stored in the non-volatile memory, recorder device 10 does not need standby power to preserve the information in stored in memory.

Example EICs

Figure 3:
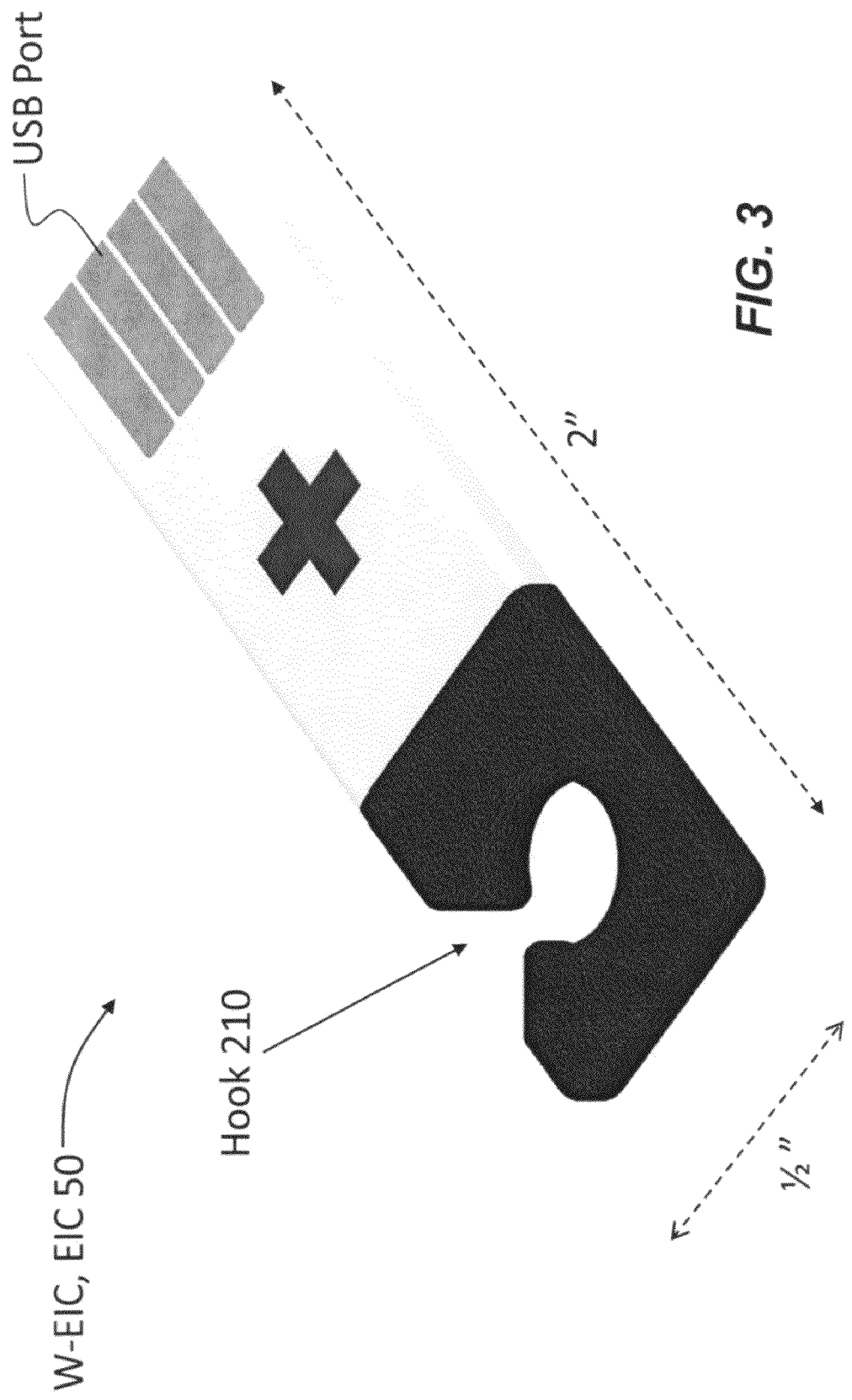
FIG. 3 is an isometric view of an example electronic information carrier (EIC) used in the recorder device of FIG. 1A and FIG. 1B.
Figure 4A:
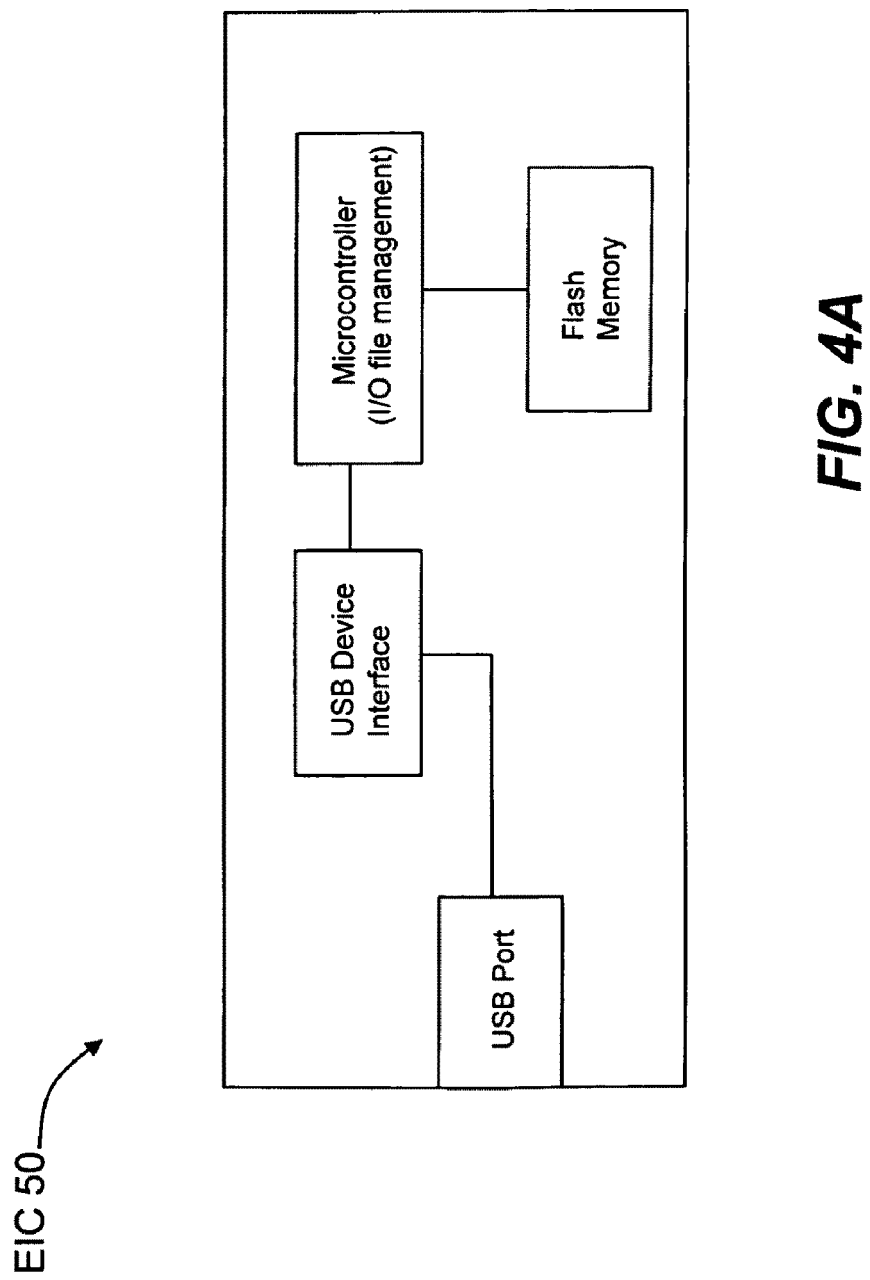
FIG. 4A is a schematic diagram of an example configuration of the EIC of FIG. 3.

FIG. 3 is an isometric view of an example EIC 50 used in recorder device 10 of FIG. 1A and FIG. 1B. FIG. 4A is a schematic diagram of an example electronic configuration for EIC 50. In an example embodiment, EIC 50 is or includes a flash memory device. EIC 50 includes a USB device interface that allows the EIC to quickly be connected to a reading device such as a host station, such as shown in FIG. 5A. In an example embodiment, EIC 50 is provided with a latch or hook 210 at one end so that the EIC can be attached to dog tags or to other parts of a person in need of medical attention. The EIC 50 can thus stay with the person so that when the person gets to the hospital or other emergency facility, the EIC can be quickly read and the person's medical information quickly extracted by the host station.

With reference to FIG. 4A, the example EIC 50 also includes a flash memory and a microcontroller. During the recording stage, data from recorder device 10 is transferred onto EIC 50 through the USB device interface. During the information uploading stage, the information is delivered to the host station through this USB device Interface (see FIG. 5). The flash memory includes, in an example embodiment, a single-chip NAND flash memory chip that can store the user's voice recording and other administrative information. A single-chip memory can hold several hours of voice data. The EIC 50 can be used multiple times, which can lead to the creation of multiple time-stamped sound files. This is useful, for instance, if a given person was treated multiple times en route to a care facility.

The microcontroller includes a built-in memory and serves to route recorded information between the USB device interface and the flash memory and can also optionally perform data encryption.

Although the EIC 50 of FIG. 4A has many advantages due to its simplicity and low-cost, a low-power wireless communication with the host station may be desirable in certain circumstances. If this requirement turns out to be necessary, the EIC design can be upgraded to include a low-power wireless interface.

Figure 4B:
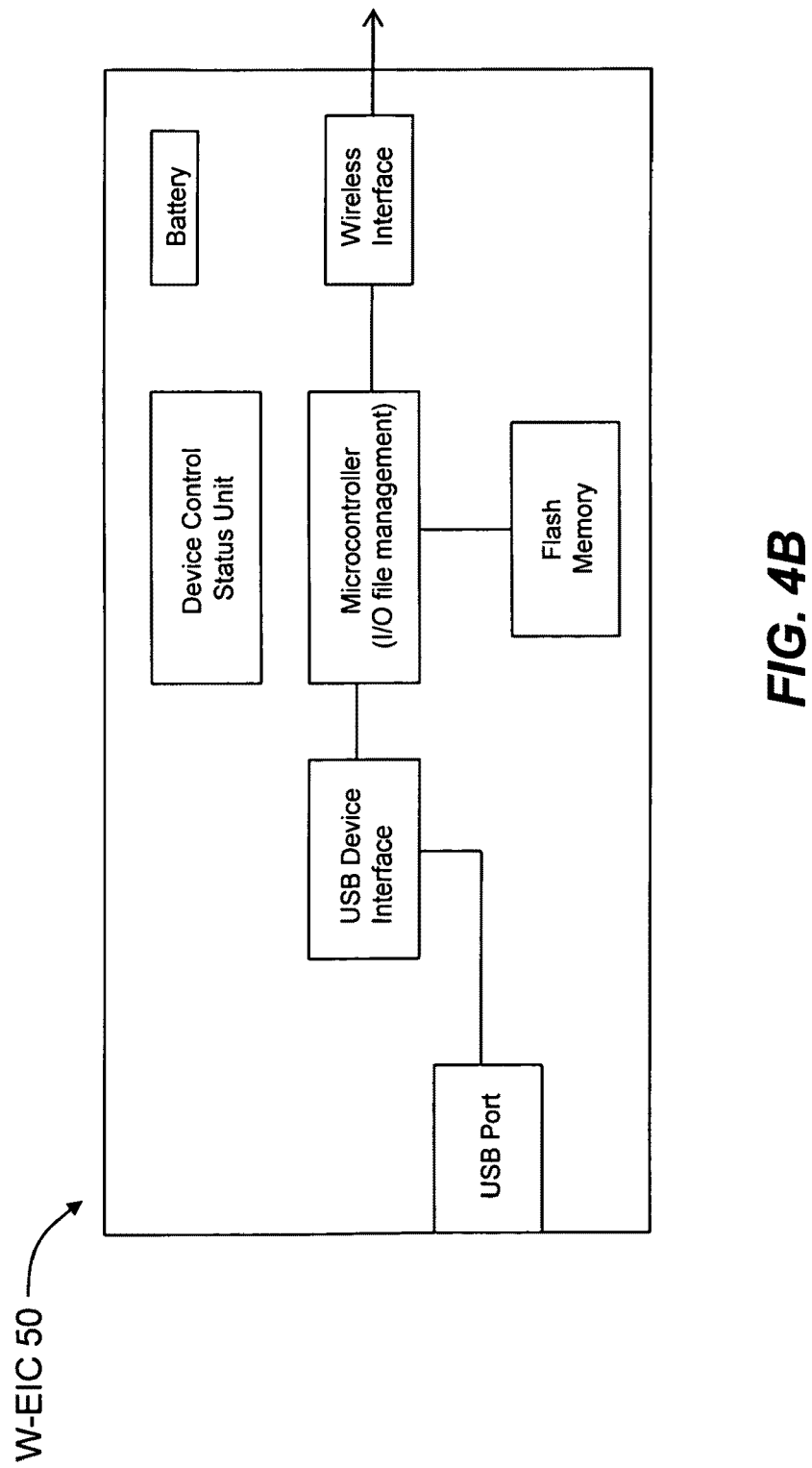
FIG. 4B is a schematic diagram of an example configuration of a wireless version of the EIC ("W-EIC") of FIG. 3.

FIG. 4B illustrates an example EIC 50 similar to that of FIG. 4A and illustrates an example embodiment of a wireless EIC ("W-EIC") 50. The W-EIC 50 is similar to EIC 50 and further includes a wireless interface, a device control status unit and a battery.

Figure 7:
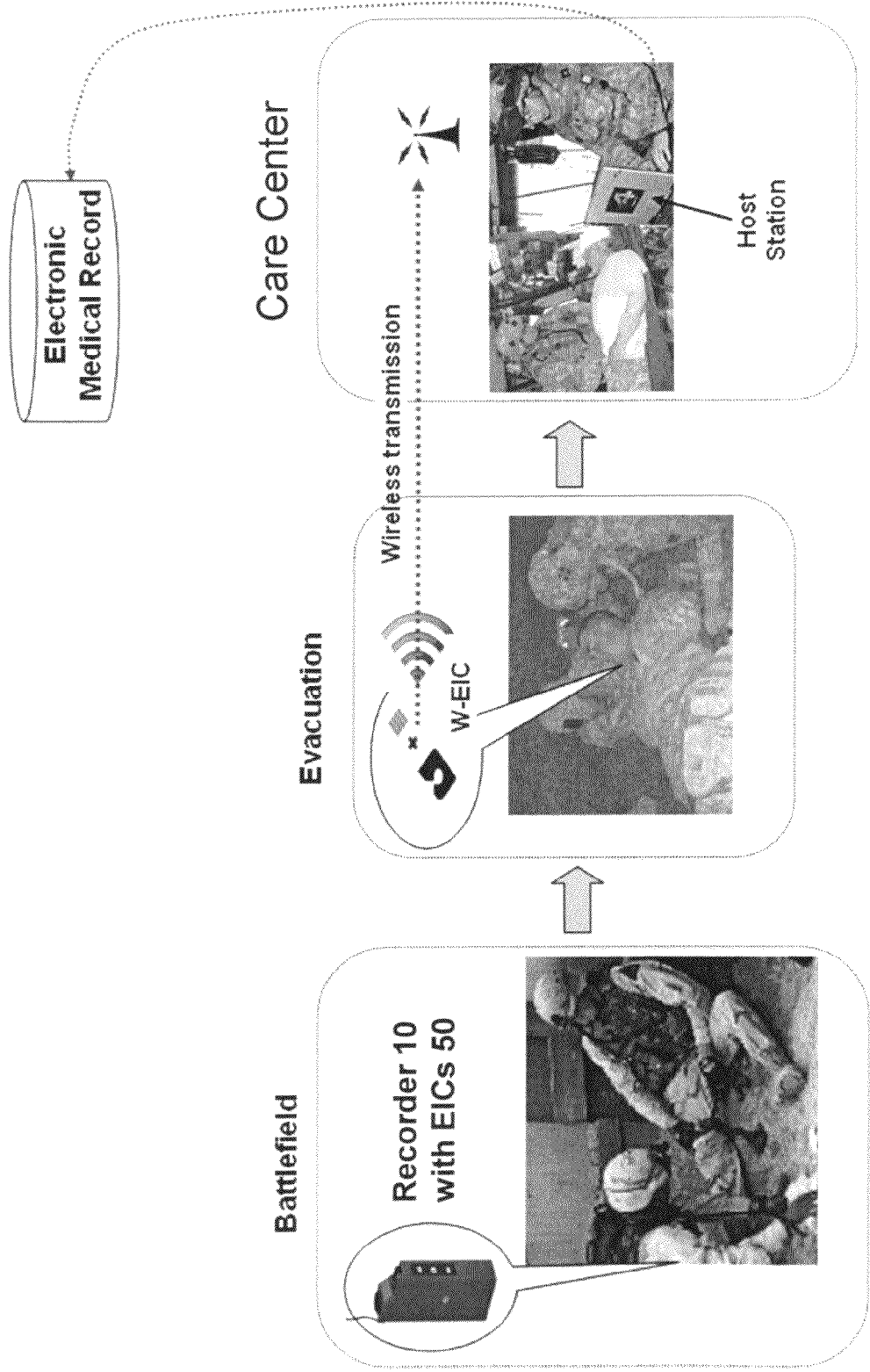
FIG. 7 is similar to FIG. 6B and illustrates an example embodiment of the information recording, transportation and readout process using a W-EIC.

The wireless interface is used to transmit recorded information to the host station, preferably while the injured person is en route to the care facility, as illustrated in FIG. 5B and FIG. 7, discussed below. The wireless interface is preferably a low-power interface such as those implemented in mobile devices and MC4 laptops. The data in the non-volatile flash memory can be routed through either the wireless interface or the USB interface. The wireless interface can be turned on or off to conserve the battery and to ensure the safety of the person being treated. Example interfaces include UWB/Wireless-USB, Bluetooth, and Wi-Fi.

In an example embodiment, the device control status unit has a fail-safe power on/off switch and Light Emitting Diodes (LEDs). The LEDs indicate if the wireless interface is turned on or off and if the wireless connection is active.

The battery is preferably a miniature rechargeable battery that provides power to the various power-consuming components of W-EIC 50. The battery is preferably rechargeable via the USB device interface The main advantage of W-EIC 50 over the non-wireless version is its ability to transmit the EIC content to the host station while en route to a care facility. The choice of wireless technology for W-EIC 50 depends on the wireless infrastructure deployed in the given environment.

MVDS Examples

Figure 6A:
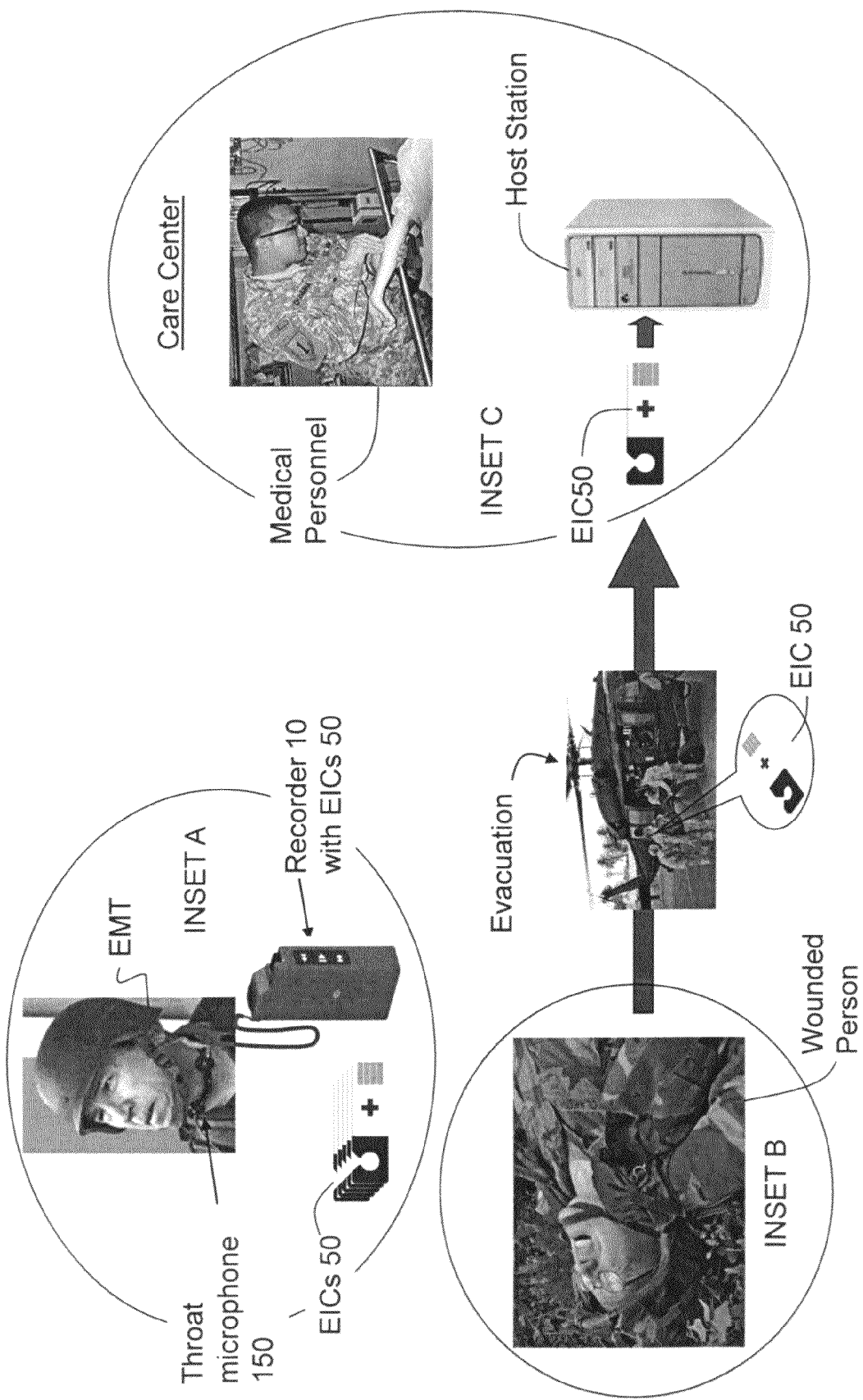
FIG. 6A and FIG. 6B are schematic depictions of how the medical recorder is used in a military environment to record information about a wounded or injured soldier and how the information is delivered to and read from a host station at a care center.
Figure 6B:
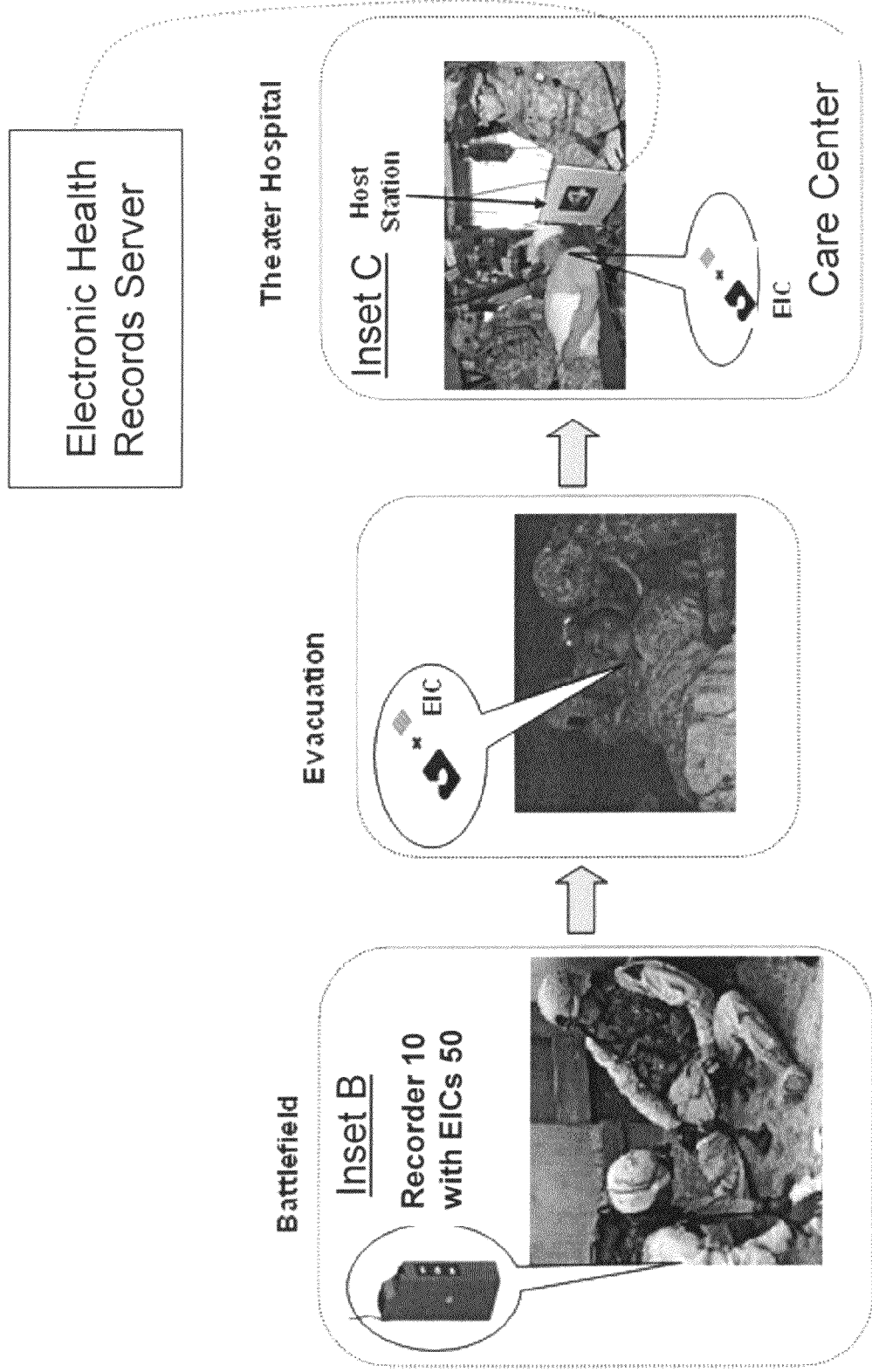

FIG. 6A and FIG. 6B are schematic depictions of the MVDS and shows how recorder device 10 is used in the MVDS system in a military environment to record information about a wounded or injured soldier and how the information is read back at the host station. The core components of the MVDS include the recorder device 10, the EIC 50, and the host station.

With reference to inset A, an EMT is provided with microphone 150, which is attached to recorder device 10. Recorder device 10 holds a plurality of EICs 50 as described above. With reference to inset B, a wounded soldier is examined by the EMT, and the EMT records the relevant medical information on one of the EICs 50 using recorder device 10. When the EMT is done, he or she removes the EIC and affixes it to the wounded soldier, e.g., to the soldier's dog tags. The EIC 50 thus travels with the wounded soldier as the soldier is evacuated. The EMT then moves on to another wounded soldier and repeats the recording and tagging procedure.

With reference to inset C, the wounded soldier and the recorded EIC 50 arrive at an emergency room (ER), theater hospital or like care center. There, the EIC is read by the host station, such as a computer with a USB port, as shown in FIG. 5A. This allows the medical personnel at the care center to quickly have access to the information recorded by the user on EIC 50 and make the appropriate medical decisions for the injured soldier.

W-EIC 50 can also be used when the injured person is en route to or arrives at the care facility to accelerate the communication of information from the W-EIC 50 to the host station. FIG. 7 is a schematic depiction of how recorder device 10 is used as part of the MVDS in a military environment to record information about a wounded or injured soldier and how the information is wirelessly transmitted to the host station at any time when such wireless transmission is possible, such as en route to the care facility, or upon arrival at the care facility. In an example embodiment, all wireless transmissions from W-EIC 50 conform to the security requirements of FIPS and HIPAA.

Host Station with MVP Software

Figure 5C:
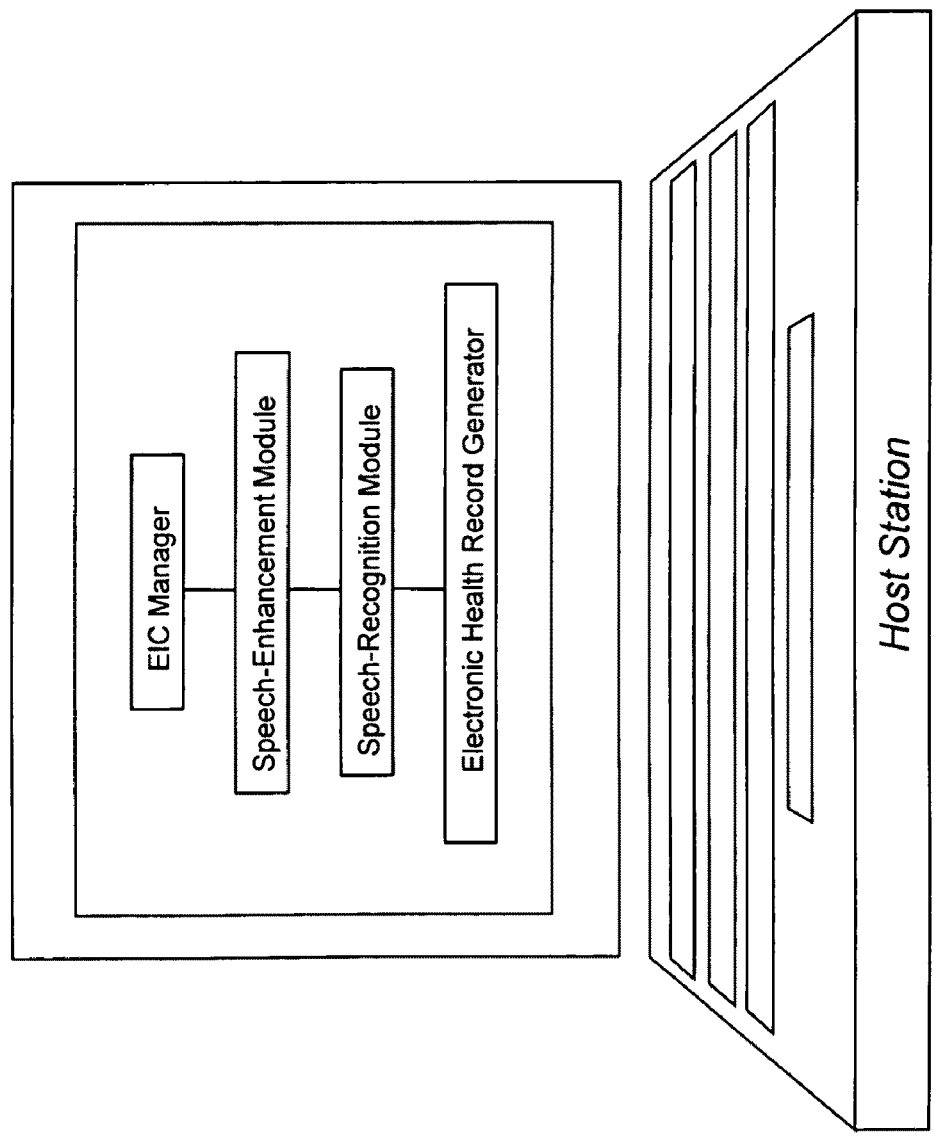
FIG. 5C is a schematic diagram of the host station and the four major components in the MVP software that runs on the host station.

In an example embodiment, the host station is or includes a general purpose computer running Medic Voice Processor (MVP) software to convert the medic's voice record to an FMC record. FIG. 5A and FIG. 5B illustrate an example host stations in the form of a lap top and a personal computer respectively. In FIG. 5A, the host station receives the EIC 50 at a USB port, while in FIG. 5B the host station has a wireless card for receiving wireless signals from W-EIC 50. FIG. 5C is a schematic diagram that illustrates the MVP software components of the host station.

Host computer includes the MC4 infrastructure so that the medical records can be up/down-loaded to/from appropriate Electronic Health (Medical) Record servers such as TMDS or CSR. The host station typically has a number of active USB ports where EICs can be plugged in: The host station is normally located in a care facility, such as BAS and Theater Hospitals. Since several injured soldiers may arrive at the care facility at the same time, the MVDS preferably includes a number of host stations in the care facility. In addition, any MC4 laptop may become the host station (see FIG. 5A and FIG. 5C) by simply installing the MVP software on it. This allows voice-to-FMC conversion and advance transmission of the FMC (or the sound files) to the care facility during long evacuation situations.

MVP is an application software package that runs on a MC4 computer platform (Windows OS). The purpose of the MVP is to convert sound files in the EIC 50 into structured medical information that can be put in the theater and DoD Electronic Medical Record with minimum user intervention. The MVP package can be installed in any MC4 computer running Windows. The MC4 infrastructure is necessary to interface with the Electronic Health Record Servers (see FIG. 7) such as TMDS or CDR.

With reference again to FIG. 5C, there are four major components in the MVP software: The EIC Manager, the Speech-Enhancement Module, the Speech-Recognition Module, and the Electronic Health Record Generator. The EIC Manager recognizes the EIC and retrieves the sound files from the EIC through the USB device interface. It organizes the files according to the timestamps, identifies the correct sound files to process, performs format conversions, and sends them to the Speech Enhancement Module. This is primarily custom-developed software with Windows drivers. If W-EIC 50 is used, then the EIC Manager performs the automatic detection of the EICs, establishes connections to it, and retrieves the data from the EIC. All data management and transmissions conform to the Department of Defense (DoD) security requirements.

Figure 9A:
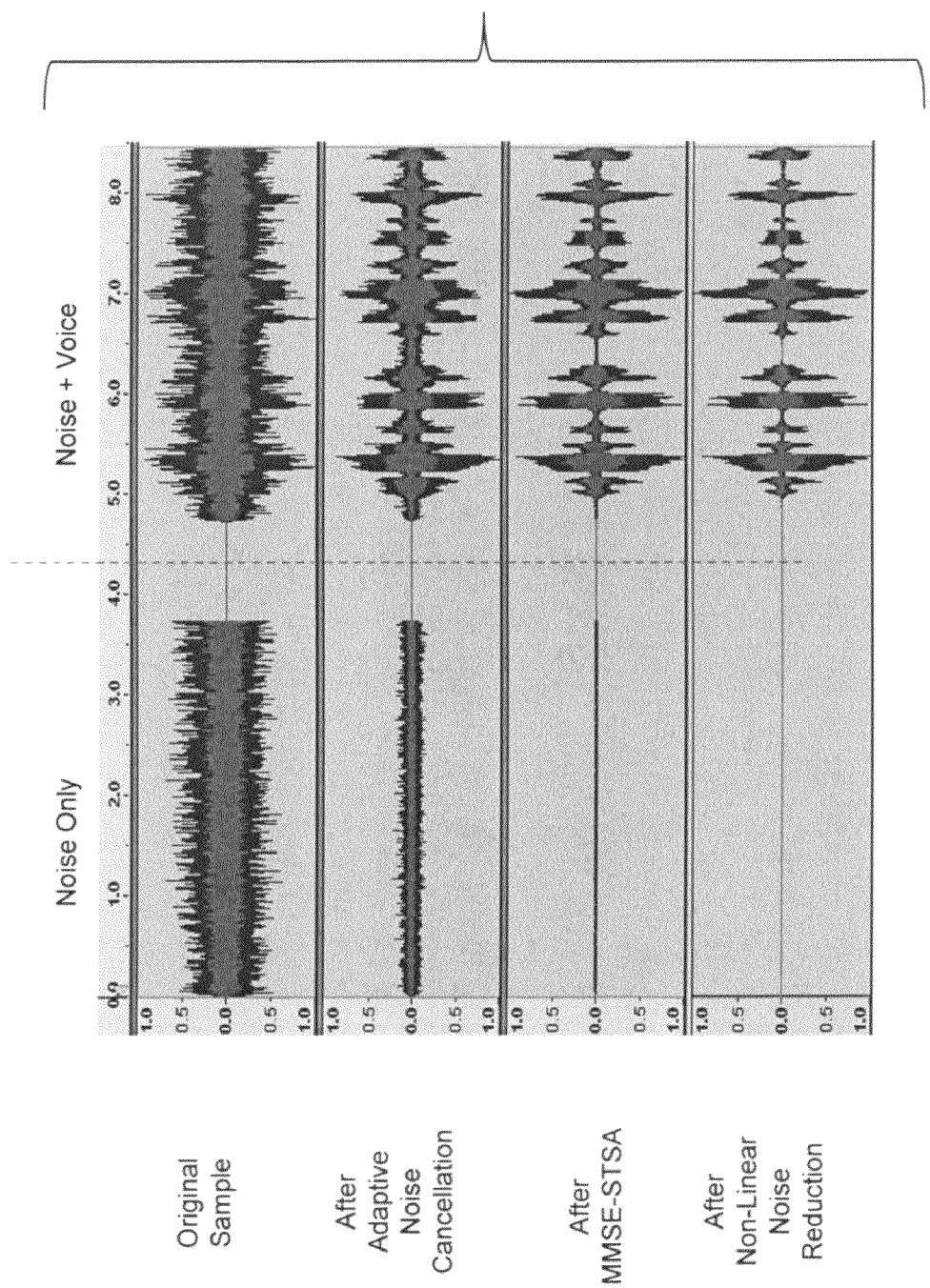

The Speech Enhancement Module uses various adaptive filters to remove the residual noise present in the sound signal and to improve the intelligibility of the speech by the Speech Recognition module. This is primarily custom-developed digital signal processing software. A 15 dB noise reduction, beyond that provided by the noise cancelling microphone, is possible in near-real time using standard desktop computers. FIG. 9A illustrates an example where noise cancellation is applied to original recording samples that include noise and noise plus voice information.

The Speech Recognition Module uses statistical models to convert the sound signal into text (words and phrases). This Module can be based on existing speech-to-text engines like Dragon NaturallySpeaking or Windows Vista/7 speech to text engine. The speech recognition needs to be speaker-independent and highly accurate. High-accuracy speech-to-text conversion requires high computational power. In the present invention, this conversion happens on the host station at the backend processing of the records so that computational power is not an issue. An interactive multimedia editing session can be useful to complete the conversion process.

The speech recognition performance can be significantly improved if the vocabulary is limited and keywords are defined. Since the purpose of the recording is to compose a field medical card such as DD1380 that has well defined structure with limited (less than 30 fields), a well structured medic training program based on keyword lexicon can make the speech recognition very reliable.

The Electronic Health Record Generator converts the text data from the Speech Recognition Module into an electronic health record. This module understands the semantics of the text stream as a simple natural language and maps the meaning into the desired record schema. The natural language query feature of commercial database systems is an example. The record schema will be compatible with digital version of DD 1380. The latter schema will enable easy synchronization and import of the data into ATHLA-T, and will let medical professionals to record, store and transfer medical records to TMDS or CDR. The latter feature will require the medics in the field to use specific keywords such as "injury" or "location" to record the description of the injury and will impose vocabulary limitations for medic. The natural language query feature of commercial database systems is an example.

Written Information Conversion

In certain situations, a user may be required to fill out a medical-related form that includes information about the person being treated. It is often desirable that the information on this form be carried along with the person as the person is transported. However, since the person will have an EIC 50 attached to him or her, it would be desirable to include an electronic version of the paper form on the EIC.

Figure 8:
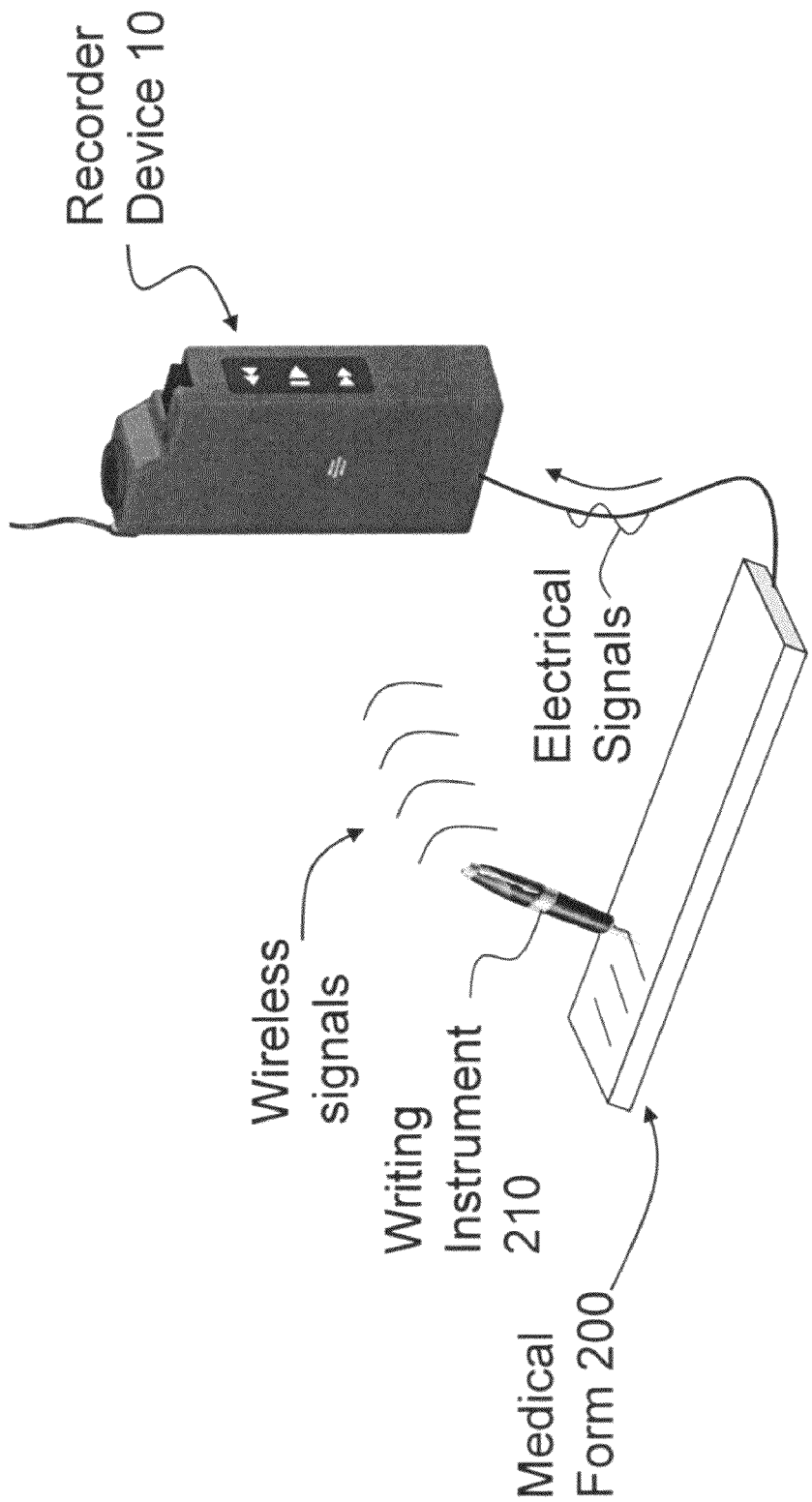
FIG. 8 is a schematic diagram of an example where information written by the user on a medical form is transferred to the recorder device either by wire or wirelessly and the information stored on the EIC.

FIG. 8 is a schematic diagram of an example embodiment where the user fills out a medical form 200 with a writing instrument 210. The medical form 200 can be a standard paper form, a reusable form (e.g., plastic), or an electronic device (i.e., an "electronic medical form") that converts written text into electronic text. In an example embodiment, a writing instrument 210 in the form of a digital pen is used, whereby the digital pen converts the written information into digital form and transmits it to recording device 10, which then transfers the information to EIC 50. In this example, recording device 10 includes a wireless interface, as shown in FIG. 2 (dashed-line box). An example digital pen and paper system for use as the writing instrument and medical form respectively is available from Anoto Group AB, in Lund, Sweden. The writing instrument or the (electronic) medical form can also be connected directly to a data port associated with recorder device electronics 100 (see dashed-line box, FIG. 2) rather than using a wireless connection.

Noise Cancellation

In many environments where people are likely to be in need of medical attention, there will be background noise that can interfere with the recording process. For example, a battlefield will often have gun fire and explosions. Also, urban areas or disaster areas will typically have noise pollution, sirens, other people shouting, etc. Thus, in an example embodiment, recording electronics 100 is configured with noise cancellation capability so that the EMT's recorded speech can be extracted from all of the recorded sound.

FIGS. 9A and 9B present a series of speech audio charts associated with recording medical information in a military environment. FIG. 9B includes gun fire and explosions as background noise. Using noise cancellation software embodied in a computer readable medium in recording electronics 100, the user's speech (and thus the relevant medical information) can be extracted in the presence of background noise from gunfire, explosions, and other background noise.

It will be apparent to those skilled in the art that various modifications and variations can be made to the present invention without departing from the spirit and scope of the invention. Thus it is intended that the present invention cover the modifications and variations of this invention provided they come within the scope of the appended claims and their equivalents.

What is claimed is:

1. A hand-held recording device for recording medical information from a user that is examining a person in an extreme environment, comprising:
    a housing having an outside and that defines an interior;
    a plurality of electronic information carriers (EICs) stored within the housing interior and capable of being dispensed therefrom, wherein the housing is configured with a spring-loaded shelf that moves a second one of the EICs into a recording position when a first one of the EICs residing in the recording position is dispensed;
    recording electronics stored within the housing interior and operably connected to whichever of the EICs is in the recording position;
    a microphone operably connected to the recording electronics to record, on the EIC in the recording position, medical information from the user about the person being examined; and
    one or more control buttons electrically connected to the recording electronics and configured to control one or more operations of the recording device.

2. The device of claim 1, wherein the recording electronics are configured to perform voice-activated recording.

3. The device of claim 1, wherein the housing is made of KEVLAR.

4. The device of claim 1, wherein each EIC comprises a flash memory and a USB port.

5. The device of claim 1, wherein each EIC further includes:
    a wireless interface configured to transmit a wireless signal; and
    at least one battery.

6. The device of claim 1, wherein the recording electronics are configured to cancel or suppress background noise.

7. The device of claim 1, wherein the EIC includes a hook configured to facilitate attaching the EIC to the injured person.

8. A medic voice data system, comprising:
    the recording device of claim 1; and
    a host station adapted to receive information from each EIC by either wireless signals generated by the EIC or via electrical signals generated by the EIC and transmitted through a USB port.

9. The system of claim 8, wherein the host station is adapted to convert a voice record into a medical record.

10. The system of claim 9, wherein the host station includes instructions embodied in a computer readable medium that cause the host station to convert the voice record into the medical record.

11. The system of claim 1, further comprising a medical form and a writing instrument, wherein at least one of the medical form and writing instrument is configured to convert written information to electronic information and transmit the electronic information to the recording electronics for storage in the at least one EIC.

* * * * *

UNITED STATES PATENT AND TRADEMARK OFFICE
CERTIFICATE OF CORRECTION

PATENT NO. : 8,233,631 B2
APPLICATION NO. : 12/798974
DATED : July 31, 2012
INVENTOR(S) : Audrius Berzanskis It is certified that error appears in the above-identified patent and that said Letters Patent is hereby corrected as shown below:

IN THE SPECIFICATION

COL. 1, LINE 10, please enter the following section heading and paragraph before the FIELD section heading:

STATEMENT OF GOVERNMENT INTEREST

This invention was made with Government support under Contract No. W31P4Q-10-C-0208 awarded by DARPA. The Government has certain rights in this invention Signed and Sealed this
Third Day of May, 2016

Michelle K. Lee
*Director of the United States Patent and Trademark Office*